(12) United States Patent
Li et al.

(10) Patent No.: US 12,303,436 B2
(45) Date of Patent: May 20, 2025

(54) ORTHOPEDIC SPINAL INJURY THERAPY DEVICE

(71) Applicant: The First People's Hospital of Yunnan Province, Kunming (CN)

(72) Inventors: Weichao Li, Kunming (CN); Weibing Liu, Kunming (CN); Tingting Dong, Kunming (CN); Xuesong Zhang, Kunming (CN); Qianbo Fan, Kunming (CN); Feilong Bao, Kunming (CN)

(73) Assignee: The First People's Hospital of Yunnan Province, Kunming (CN)

( * ) Notice: Subject to any disclaimer, the term of this patent is extended or adjusted under 35 U.S.C. 154(b) by 423 days.

(21) Appl. No.: 17/845,250

(22) Filed: Jun. 21, 2022

(65) Prior Publication Data

US 2022/0401280 A1    Dec. 22, 2022

(30) Foreign Application Priority Data

Jun. 22, 2021    (CN) .......................... 202121386508.1

(51) Int. Cl.
*A61G 13/12*    (2006.01)
*A61G 13/00*    (2006.01)
(Continued)

(52) U.S. Cl.
CPC ....... *A61G 13/009* (2013.01); *A61G 13/1225* (2013.01); *A61G 13/1265* (2013.01); *A61G 7/05723* (2013.01); *A61G 13/128* (2013.01); *A61G 2200/327* (2013.01); *A61M 35/30* (2019.05)

(58) Field of Classification Search
CPC . A61M 35/30; A61G 13/009; A61G 13/1225; A61G 13/123; A61G 13/1265; A61G 13/128; A61G 7/05723
See application file for complete search history.

(56) References Cited

U.S. PATENT DOCUMENTS 6,190,338 B1 *    2/2001   Arndt ................... A61G 13/009
                                                        601/102
6,684,095 B1 *    1/2004   Bonutti ................. A61G 13/12
                                                        5/624
(Continued)

FOREIGN PATENT DOCUMENTS

CN            112353593 A    *   2/2021

*Primary Examiner* — Keri J Nelson
(74) *Attorney, Agent, or Firm* — John H. Choi & Associates

(57) ABSTRACT

An orthopedic spinal injury therapy device. The device comprises a lying plate, an inflatable bag is provided in the middle of the lying plate, a straight slot is formed in one side of the inflatable bag, supporting plates are vertically connected to both sides of the bottom end of the lying plate, a sliding rod is horizontally arranged between the supporting plates, a nut block and a movable block are connected to both ends of the sliding rod respectively, a threaded rod is vertically connected into the nut block, a fixed rod vertically penetrates through the movable block; the upper ends and the lower ends of the threaded rod and the fixed rod are fixed to side walls of the corresponding supporting plates by mounting blocks, a hollow-square sliding block is slidingly provided on the sliding rod, and a mounting plate is connected to the top of the sliding block.

5 Claims, 2 Drawing Sheets

(51) Int. Cl.
*A61G 7/057* (2006.01)
*A61M 35/00* (2006.01)

(56) References Cited

U.S. PATENT DOCUMENTS 8,661,591 B1 * 3/2014 Sonderland .......... A47C 27/146
　　　　　　　　　　　　　　　　　　　　5/733
2022/0047840 A1 * 2/2022 Lee ..................... C04B 33/32

* cited by examiner

ORTHOPEDIC SPINAL INJURY THERAPY DEVICE

CROSS REFERENCE TO RELATED APPLICATION

This patent application claims the benefit and priority of Chinese Patent Application No. 202121386508.1, filed on Jun. 22, 2021, the disclosure of which is incorporated by reference herein in its entirety as part of the present application.

TECHNICAL FIELD

The present disclosure relates to the technical field of medical devices, and in particular relates to an orthopedic spinal injury therapy device.

BACKGROUND ART

The recovery of spinal injuries requires physical therapy as well as pharmacotherapy. However, most of the existing orthopedic spinal injury therapy devices only have a single function and are incapable of meeting various therapeutic schedules.

In order to solve the problem above, an orthopedic spinal injury therapy device is provided.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An objective of the present disclosure is to provide an orthopedic spinal injury therapy device to solve the defects in the prior art.

To achieve the objective, the present disclosure adopts the following technical solutions:

An orthopedic spinal injury therapy device comprises a lying plate, wherein an inflatable bag is provided in the middle of the lying plate, a straight slot is formed in one side of the inflatable bag, supporting plates are vertically connected to both sides of the bottom end of the lying plate, a sliding rod is horizontally arranged between the supporting plates, a nut block and a movable block are connected to both ends of the sliding rod respectively, a threaded rod is vertically connected into the nut block by threads, and a fixed rod vertically penetrates through the movable block; the upper ends and the lower ends of the threaded rod and the fixed rod are fixed to side walls of the corresponding supporting plates by mounting blocks, a hollow-square sliding block is slidingly provided on the sliding rod, and a mounting plate is connected to the top of the sliding block; fixed blocks are arranged at four right-angle sides of the top end surface of the mounting plate, pull rods vertically penetrate through the fixed blocks, and chucks are connected the ends, close to each other, of the pull rods.

Preferably, a motor is connected to the bottom end of the threaded rod.

Preferably, the chuck is designed as a transverse concave structure.

Preferably, a fastening bolt is vertically connected to the bottom of the sliding block, and the fastening bolt abuts against the lower end surface of the sliding rod.

Preferably, the pull rod between the fixed block and the chuck is sleeved with a spring.

The present disclosure has the beneficial effects that:

1. In accordance with the present disclosure, a patient lies on the lying plate, a fumigation therapy box is placed on the mounting plate for fumigation therapy of spine part; during acupuncture, a mirror can be placed on the mounting plate to facilitate the observation of back conditions, thus satisfying implementation of various therapeutic schedules;

2. In accordance with the present disclosure, the inflatable bag is provided at the lumbar vertebra position for supporting, thus avoiding lumbar vertebra injury. A position of the mounting plate can be adjusted by the sliding block and fixed by the fastening bolt, and the providing of the threaded rod and the fixed rod can enable the sliding rod to move up and down through the corresponding nut block and the corresponding movable block, thus meeting various requirements.

BRIEF DESCRIPTION OF THE DRAWINGS

The foregoing summary, as well as the following detailed description of presently preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Figure 1:
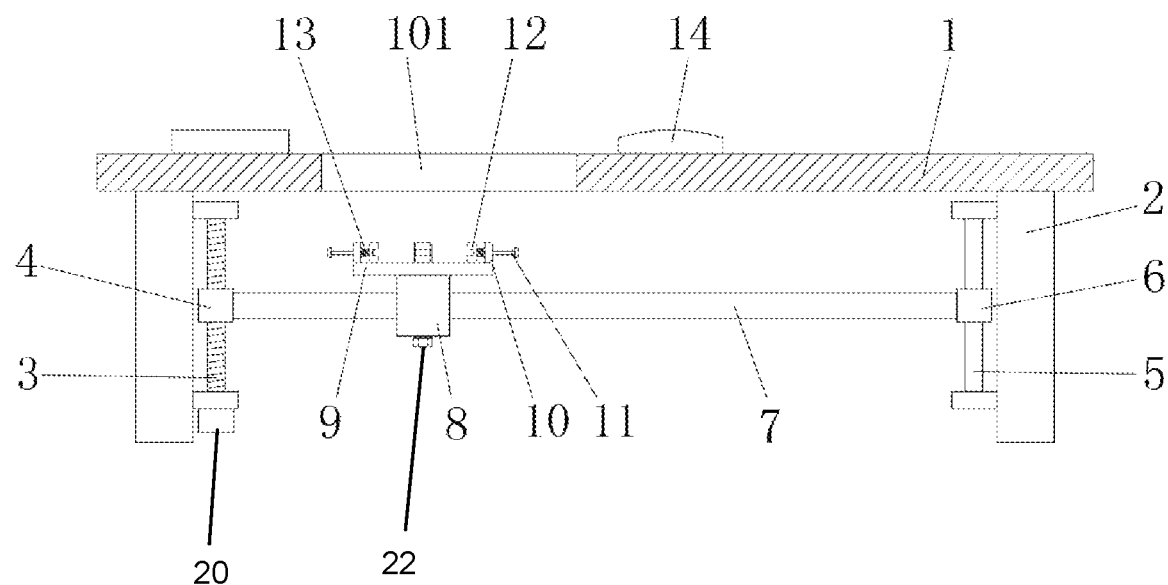
FIG. 1 is a front-view structure diagram of an orthopedic spinal injury therapy device provided by the present disclosure.

To facilitate an understanding of the invention, identical reference numerals have been used, when appropriate, to designate the same or similar elements that are common to the figures. Further, unless stated otherwise, the features shown in the figures are not drawn to scale and are shown for illustrative purposes only.

In the drawings: 1—lying plate; 101—straight slot; 2—supporting plate; 3—threaded rod; 4—nut block; 5—fixed rod; 6—movable block; 7—sliding rod; 8—sliding block; 9—mounting plate; 10—fixed block; 11—pull rod; 12—chuck; 13—spring; 14—inflatable bag; 20—motor; 22—fastening bolt.

DETAILED DESCRIPTION OF THE EMBODIMENTS

The following clearly and completely describes the technical solutions in the embodiments of the present disclosure with reference to the accompanying drawings in the embodiments of the present disclosure. The described embodiments are merely a part rather than all of the embodiments of the present disclosure.

Certain terminology is used in the following description for convenience only and is not limiting. The article "a" is intended to include one or more items, and where only one item is intended the term "one" or similar language is used.

Additionally, to assist in the description of the present invention, words such as top, bottom, side, upper, lower, front, rear, inner, outer, right and left are used to describe the accompanying figures. The terminology includes the words above specifically mentioned, derivatives thereof, and words of similar import.

Figure 2:
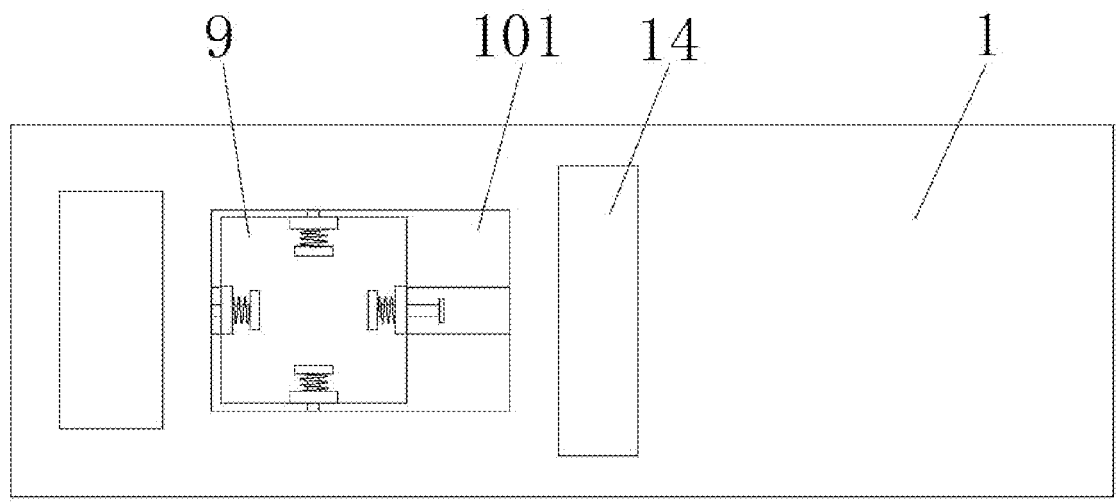
FIG. 2 is a top-view structure diagram of an orthopedic spinal injury therapy device provided by the present disclosure.
Figure 3:
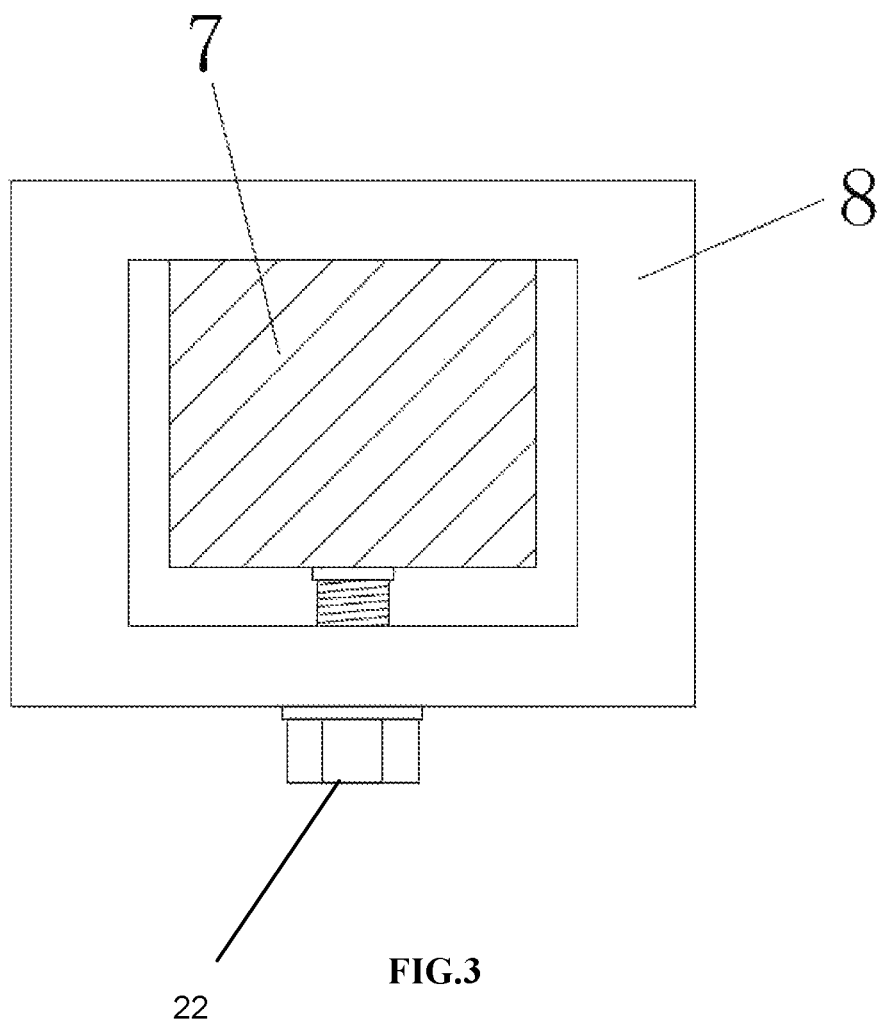
FIG. 3 is a side-view structure diagram of a sliding block in an orthopedic spinal injury therapy device provided by the present disclosure.

In this embodiment, referring to FIG. 1 to FIG. 3, an orthopedic spinal injury therapy device comprises a lying plate 1, wherein an inflatable bag 14 is provided in the middle of the lying plate 1, a straight slot 101 is formed in one side of the inflatable bag 14, supporting plates 2 are vertically connected to both sides of the bottom end of the lying plate 1, a sliding rod 7 is horizontally arranged between the supporting plates 2, a nut block 4 and a movable block 6 are connected to both ends of the sliding rod 7 respectively, a threaded rod 3 is vertically connected into the nut block 4 by threads, and a fixed rod 5 vertically penetrates through the movable block 6; the upper ends and the lower ends of the threaded rod 3 and the fixed rod 5 are fixed to the side walls of the corresponding supporting plates 2 by mounting blocks, a hollow-square sliding block 8 is slidingly provided on the sliding rod 7, and a mounting plate 9 is connected to the top of the sliding block 8; fixed blocks 10 are arranged at four right-angle sides of the top end surface of the mounting plate 9, pull rods 11 vertically penetrate through the fixed blocks 10, and chucks 12 are connected to the ends, close to each other, of the pull rods 11.

A motor 20 is connected to the bottom end of the threaded rod 3. The chuck 12 is designed as a transverse concave structure. A fastening bolt 22 is vertically connected to the bottom of the sliding block 8, and the fastening bolt 22 abuts against the lower end surface of the sliding rod 7. The pull rod 11 between the fixed block 10 and the chuck 12 is sleeved with a spring 13.

In a specific embodiment: the device is an orthopedic spinal injury therapy device. During use, a patient needs to lie on the lying plate 1, the lumbar vertebra of the patient can be on the inflatable bag 14 which is inflated with a proper amount of gas to provide enough support for the lumbar vertebra, thus avoiding lumbar vertebra injury. The spine part of the patient is located on the straight slot 101, a fumigation therapy box can be placed on the mounting plate 9 below the straight slot 101 and clamped by the chucks 12, then the fumigation therapy box is moved to the position of the straight slot 101 to fumigate the spine part. When the spine part of the patient is acupunctured, a mirror can be stably clamped into concave clamping grooves of the chucks 12 on the mounting plate 9 to facilitate the observation of back conditions, thus meeting the demands of various therapeutic schedule. In addition, when the therapy is not needed, a thick pillow can be placed on the mounting plate 9 for filling the straight slot 101, thus providing enough support for the back when the patient lies on the lying plate 1 and improving the therapy effect.

The above is only a better specific embodiment of the present disclosure, but the scope of protection of the present disclosure is not limited thereto. The equivalent replacement or changes made by any person skilled in the art in the technical scope disclosed by the present disclosure according to the technical solutions of the present disclosure and the concept of the present disclosure shall be encompassed within the scope of protection of the present disclosure. The scope of the invention will be, therefore, indicated by claims rather than by the foregoing description.

The invention claimed is:

1. An orthopedic spinal injury therapy device, comprising:
   a lying plate (1), wherein an inflatable bag (14) is provided in the middle of the lying plate (1);
   a straight slot (101) formed in the lying plate (1) on one side of the inflatable bag (14);
   supporting plates (2) vertically connected to both sides of the bottom end of the lying plate (1);
   a sliding rod (7) having opposing ends, the sliding rod horizontally arranged between the supporting plates (2);
   a nut block (4) and a movable block (6) connected to the opposing ends of the sliding rod (7):
   a threaded rod (3) vertically connected into the nut block (4) by threads and a fixed rod (5) vertically penetrating through the movable block (6), wherein upper ends and lower ends of the threaded rod (3) and the fixed rod (5) are fixed to side walls of the corresponding supporting plates (2) by mounting blocks;
   a hollow-square sliding block (8) slidingly provided on the sliding rod (7), and a mounting plate (9) connected to a top portion of the sliding block (8);
   fixed blocks (10) positioned at four right-angle sides of a top end surface of the mounting plate (9); and
   pull rods (11) vertically penetrating through the fixed blocks (10), and chucks (12) connected to ends of the pull rods (11).

2. The orthopedic spinal injury therapy device according to claim 1, wherein a motor (20) is connected to a bottom end of the threaded rod (3).

3. The orthopedic spinal injury therapy device according to claim 1, wherein each of the chucks (12) is a transverse concave structure.

4. The orthopedic spinal injury therapy device according to claim 1, wherein a fastening bolt (22) is vertically connected to a bottom of the sliding block (8), and the fastening bolt abuts against a lower end surface of the sliding rod (7).

5. The orthopedic spinal injury therapy device according to claim 1, wherein each of the pull rods (11) between the respective fixed block (10) and the respective chuck (12) is sleeved with a spring (13).

* * * * *